United States Patent [19]

Samour et al.

[11] 3,959,355

[45] May 25, 1976

[54] MONOMERIC EMULSION STABILIZERS DERIVED FROM ALKYL/ALKENYL SUCCINIC ANHYDRIDE

[76] Inventors: Carlos M. Samour, 324 Linden St., Wellesley, Mass. 02181; Mildred C. Richards, 32 W. Park Drive, Wakefield, Mass. 01880

[22] Filed: June 6, 1974

[21] Appl. No.: 476,950

Related U.S. Application Data

[60] Division of Ser. No. 309,038, Nov. 24, 1972, Pat. No. 3,839,419, which is a division of Ser. No. 40,718, May 26, 1970, Pat. No. 3,751,451, which is a continuation-in-part of Ser. No. 867,900, Oct. 20, 1969, abandoned.

[52] U.S. Cl. .................. 260/482 R; 260/459 A; 260/470
[51] Int. Cl.² .................................... C07C 101/06

[58] Field of Search ......... 260/485 H, 482 R, 485 J, 260/459 A, 470

[56] References Cited
UNITED STATES PATENTS
3,787,474    1/1974    Daniels et al. ................. 260/482 R Primary Examiner—Lorraine A. Weinberger
Assistant Examiner—Jane S. Myers
Attorney, Agent, or Firm—Ellen P. Trevors

[57] ABSTRACT

Quaternary ammonium salts having a lipophilic group covalently linked to the quaternary nitrogen through hydroxysuccinyloxy or hydroxysuccinylamino radicals are disclosed. These quaternary ammonium salts are useful as monomeric emulsion stabilizers.

3 Claims, No Drawings

MONOMERIC EMULSION STABILIZERS DERIVED FROM ALKYL/ALKENYL SUCCINIC ANHYDRIDE

This is a division of application Ser. No. 309,038 filed Nov. 24, 1972, now U.S. Pat. 3,839,419, which is a division of application Ser. No. 40,718, filed May 26, 1970, now U.S. Pat. 3,751,451 issued Aug. 7, 1973, which in turn is a continuation-in-part of application Ser. No. 867,900, filed Oct. 20, 1969, now abandoned.

This invention relates to stabilizing agents for emulsion polymerization. More particulaly it relates to a class of quaternized organic salts which serve simulataneously as stabilizing agents for emulsion polymerizations and as monomeric reactants in the polymerization, so that the salts become an integral part of the polymer, which is thereby self-stabilized without the use of surfactants.

Polymeric latices, derived from ethylenically-unsaturated monomers, are widely used for a variety of applications, such as adhesive masses and binders for nonwoven fabrics. Most conventional polymeric latices are produced by an emulsion polymerization process, in which monomeric materials are polymerized while they are dispersed in an aqueous medium by means of a surface active agent. The surface active agent may be anionic in nature, such as soap or sodium lauryl sulfate. Alternatively, it may be of a nonionic type as represented by various ethylene oxide derivatives, or by polyhydroxy compounds or it may be cationic, as represented by alkyl ammonium halides. Cationic agents are preferably combined with a nonionic agent for improved performance. The polymerizaton of monomeric materials is also frequently effected in the presence of water-soluble protective colloids or stabilizing agents. Any of the above emulsifying or stabilizing agents leads to the presence of a water-sensitive ingredient in the final polymeric latex. For latex utilizations wherein wet strength and resistance to the influence of water are desirable, as in most paper coatings, nonwoven fabrics, certain pressure-sensitive adhesive tapes, and the like, the presence of a water-sensitive ingredient in the polymeric mass is undesirable.

A preferred method of avoiding the presence of water-sensitive elements in a polymeric latex is to employ what is termed herein monomeric emulsion stabilizers — that is, a class of organic monomer which co-polymerizes with the ethylenically-unsaturated monomers, becoming a part of the final polymer, but which stabilizes the polymerization process against the formation of coagulum and against subsequent phase separation. Such monomeric emulsion stabilizers may be cationically-charged nitrogen compounds as set forth in U.S. Pat. No. 3,399,159 wherein the use of monomers such as vinyl pyridines, acid-amines, and certain nitrogen-containing acrylic derivatives is described.

Now it has been found that selected quaternary ammonium salts wherein the quaternized nitrogen is covalently linked to a lipophilic group through a hydroxysuccinyloxy or hydroxysuccinylamino group are excellent monomeric emulsion stabilizer for the polymerization of ethylenically-unsaturated monomers.

More particularly, the compounds of this invention have the formula

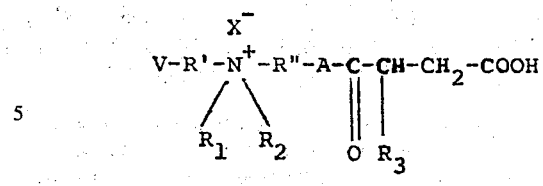

I wherein V is an ethylenically-unsaturated radical; R' is zero or a diradical; R'' is a diradical; A is oxygen or —NH—; $R_1$ and $R_2$ are independently selected alkyl, hydroxylalkyl, aryl, $R_5$—O—CO—$CH_2$— or $R_5$—NH—CO—$CH_2$— wherein $R_5$ is hydrogen or alkyl or together part of a heterocyclic amino radical in which the quaternary nitrogen atom in formula I is part of the ring; $R_3$ is a lipophilic radical comprising an aliphatic hydrocarbon group having about 7 to about 7 to about 28 carbon atoms; and $X^-$ is a halide, alkyl sulfate wherein the alkyl moiety has 1 to 4 carbon atoms or toluene sulfonate radical. Isomers of compounds I wherein the lipophilic radical R3 is attached to the carbon atom adjacent to the carboxyl group are also included in the scope of this invention.

These compounds I are readily prepared from available materials, and thus are attractive for use in commercial operations.

While any compound having the general formula I can be provided according to this invention, preferred monomeric emulsion stabilizers include these compounds I where V is an ethylenically-unsaturated radical selected from the group consisting of acryloyloxy, methacryloyloxy, acrylamido, methacrylamido, vinyloxy, alyloxy, methallyloxy, vinylacetoxy, allylacetoxy, methallylacetoxy, allyl, methallyl, and acid ester groups or acid amido groups such as 4-hydroxymaleoyloxy and 4-hydroxyfumaroyloxy (HO—CO—CH=CH—COO—), 4-hydroxymaleoylamino and 4-hydroxyfumaroylamino (HO—CO—CH=CH—CONH—), 4-hydroxycitraconoyloxy (HO—CO—CH=C(CH$_3$)—COO—), 4-hydroxycitraconoylamino (HO—CO—CH=C(CH$_3$)—CONH—), 4-hydroxyitaconoyloxy

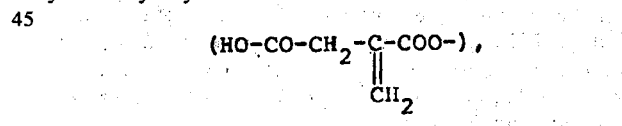

and 4-hydroxyitaconoylamino

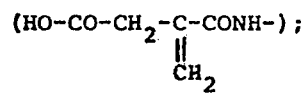

R' and R'' are independently selected ethylene, propylene, isopropylene, 2-hyroxypropylene, acetoxypropylene or —$CH_2$—$CHR_4$(O—$CH_2$—$CHR_4$)$_n$ where n is zero to 4 and $R_4$ is hydrogen or methyl; with the proviso that R' is zero where V is vinylacetoxy, allylacetoxy, methallylacetoxy, allyl, or methallyl;

A is oxygen or —NH—;

$R_1$ and $R_2$ are a. independently selected from the group consisting of alkyl having 1 to 7 carbon atoms, hydroxyalkyl having 1 to 7 carbon atoms, benzyl, $R_5$O—

CO—CH$_2$— and R$_5$—NH—CO—CH$_2$— where R$_5$ is hydrogen or alkyl having 1 to 4 carbon atoms; or
b. together part of a morpholinium or piperidinium moiety;

R$_3$ is a lipophilic aliphatic hydrocarbon group having from about 7 to about 28 carbon atoms including saturated, unsaturated, straight-chain and branched groups, and mixtures thereof; and X$^-$ is halide, e.g., fluoride, chloride, bromide, or iodide; alkyl sulfate wherein the alkyl moiety has 1 to 4 carbon atoms, or toluene sulfonate.

The monomeric emulsion stabilizers having the formula I can be synthesized by several convenient methods. For example, according to one process an alkyl or alkenyl succinic anhydride is reacted with a tertiary-amino alcohol or amine, to provide an intermediate which is subsequently reacted with a monomer containing an active halogen atom to provide compounds I wherein X$^-$ is halide. This reaction is illustrated by the following general equation wherein V, R', R'', A, and R$_3$ are as previously described.

Representative monomers having the formula VR'X include 2-bromoethyl acrylate, 2-chloroethylacrylamide, allyl chloroacetate, methallyl chloroacetate, acryloyloxypropenyl chloride, 3-methacryloyloxy, 2-hydroxypropylene chloride, acryloyloxydi(ethylenoxy)ethylene chloride, allyl bromide, methallyl chloride, etc.

The reaction to provide the monomeric emulsion stabilizers I is generally carried out at temperatures from about 0°C to about 100°C, but higher or lower temperatures can be employed. Preferably, temperatures between about 25°C and about 100°C are used.

Although the reaction proceeds readily in the absence of a solvent, diluents such as water, acetonitrile, dimethylformamide, ethyl acetate, methanol and methylene chloride can be suitably employed. Monomers such as acrylonitrile can also be utilized as solvents in the preparation of the monomeric emulsion stabilizers. While compounds I can be isolated prior to use in polymerization reactions, preferably they are used in their reaction solutions.

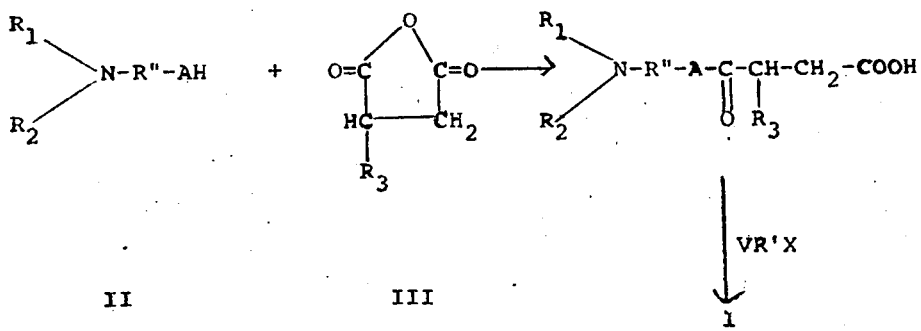

II    III

Exemplificative tertiary-amino alcohols and amines II suitable for use in the preparation of compounds I include dimethylaminoethanol, methylpropylaminopropanol, dibutylamino isopropylamine, dimethylaminoacetoxypropanol and hydroxypropyl piperidine.

The alkyl or alkenyl succinic anhydrides III are readily provided by known methods, such as by reacting maleic anhydride with an olefin as described in U.S. Pat. 2,741,597. Illustrative compounds III include heptenyl succinic anhydride, octacosasuccinic anhydride, n-heptyl succinic anhydride, iso-octadecenyl succinic anhydride, etc.

Alternately, the above-described process can be reversed by first quaternizing the tertiary-amino compound II by the monomer VR'X, followed by reaction with the alkyl or alkenyl succinic anhydride III.

Another suitable method for preparing the monomeric emulsion stabilizers having the formula I wherein X$^-$ is halide comprises quaternizing a vinyl monomer containing a tertiary-amine group by a haloalcohol or amine, followed by reaction with the alkyl or alkenyl succinic anhydride in accordance with the following general equation wherein V, R', R'', A, R$_1$, R$_2$, R$_3$ and X$^-$ are as first described.

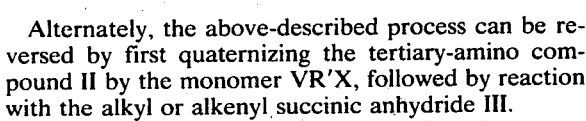

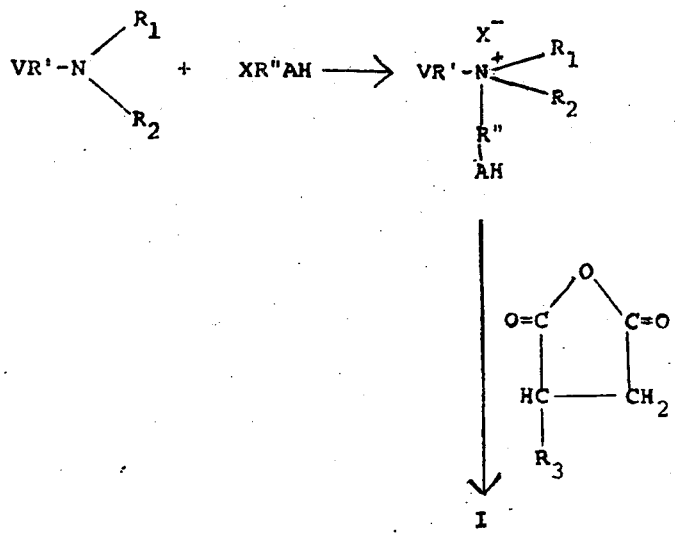

Again, as in the first process, the order of the above reaction can be reversed.

A third general procedure for the preparation of compounds I comprises the reaction of an alkyl or alkenyl succinic anhydride with a vinyl containing tertiary amino alcohol or amine followed by quaternization as illustrated by the following equation. All compounds included in formula I can be prepared by this method with the exception of those monomeric emulsion stabilizers wherein $R_1$ and $R_2$ together are part of a morpholinium or piperidinium moiety.

where $R_5$ is a hydrogen atom or a methyl group, and $R_6$ is an alkyl radical of 1 to 14, and preferably 1 to 4 carbon atoms. As is known in the art of preparing acrylic ester polymers, the softness of the polymer and the difficulty of initiating polymerization increase as the number of carbon atoms in the ester group increases. In the practice of this invention, when the acrylic monomer contains more than 8 carbon atoms in the ester group, it is advantageous to mix therewith at least about 20 mole percent of an acrylic ester with fewer than 4 carbon atoms in the ester group to initiate

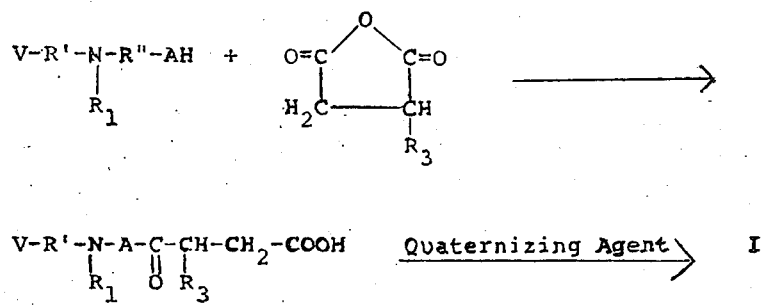

For example, vinyl containing tertiary amino alcohols such as allylbenzylaminoethanol; 4-hydroxymaleoylaminoethyl, 2-aminoethylmethylamine; etc. can be employed as starting materials in this process. Suitable quaternizing agents include dimethyl sulfate, dibutyl sulfate, methyl toluene sulfonate, ethylchloroacetate, propylchloroacetate, chloroacetamide, methyl bromide, bromoethanol, bromoheptanol, etc.

All compounds I wherein $X^-$ is alkyl sulfate in which the alkyl moiety has 1 to 4 carbon atoms, or toluene sulfonate can be provided by reacting the corresponding quaternary ammonium halide with an appropriate alkali metal salt, e.g. sodium methyl sulfate, sodium butyl sulfate, sodium toluene sulfonate, etc.

Particularly preferred monomeric emulsion stabilizers include those compounds I wherein V is allyl, methallyl, vinylacetoxy, allylacetoxy or methallylacetoxy; R' is zero; R'' is ethylene, propylene or isopropylene; A is oxygen or —NH—; $R_1$ and $R_2$ are (a) independently selected alkyl having 1 to 4 carbon atoms, or (b) together part of a morpholinium or piperidinium moiety; $R_3$ is a lipophilic aliphatic hydrocarbon group having about 7 to about 28 carbon atoms; and $X^-$ is halide; and compounds I wherein V is acryloyloxy, methacryloyloxy, vinyloxy, or 4-hydroxymaleoyl; R' and R'' are independently selected ethylene, propylene or isopropylene groups; A is oxygen; $R_1$ and $R_2$ are (a) independently selected alkyl having 1 to 4 carbon atoms; or (b) together part of a morpholinium or piperidinium moiety; $R_3$ is a lipophilic aliphatic hydrocarbon group having from about 7 to 28 carbon atoms; and $X^-$ is halide.

The monomeric emulsion stabilizers described in this invention are a new and exceptionally efficient species, promoting the smooth and ready polymerization of a wide variety of ethylenically-unsaturated monomers.

Illustrative ethylenically-unsaturated monomers suitable for copolymerizing with the monomeric emulsion stabilizers of this invention comprise vinyl acetate, vinyl chloride, acrylonitrile, and acrylic monomers in general represented by the formula

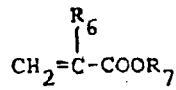

polymerization and enhance the stability of the dispersion.

Mixtures of more than one such ethylenically-unsaturated monomer may be used, and in order to impart special properties of toughness, rigidity, or cross-linking reactivity to the polymer, a minor proportion, usually less than 20 mole percent, of the major monomer may be replaced by some other ethylenically-unsaturated monomer such as vinyl esters, typified by vinyl laurate and vinyl stearate; vinyl ethers such as vinyl methyl ether, vinyl ethyl ether, and vinyl butyl ether; di-unsaturated monomers such as diethylene glycol diacrylate, ethylene glycol diitaconate, diallyl phthalate, divinyl benzene and the like; acrylic and methacrylic acids, acrylamide and methacrylamide, hydroxyethyl acrylate and methacrylate and hydroxypropyl acrylate and methacrylate, and styrene.

In general, in the polymerization process of this invention, 0.1 to 10 percent by weight of monomeric emulsion stabilizer is employed, with 1 to 5 percent by weight being preferred. The amount of monomeric emulsion stabilizer is based on the total monomers added to the polymerization reaction.

Aqueous polymeric dispersions may be prepared according to this invention in which the solid polymer content is 40% to 50% by weight. If desired, the solids content may be diluted to 1% by weight or less, with excellent retention of stability at both the higher and lower concentrations.

The monomeric emulsion stabilizers of this invention are useful in both batch and continuous polymerization processes.

The following examples will serve to illustrate the practice of this invention.

EXAMPLE 1

Allyl chloride (7.7g.) was added gradually at 25°C to a solution of 8.9g. of dimethylaminoethanol in 16.6g. of acetonitrile. The resulting clear solution was maintained at 25°C for 25 hours; at the end of this period the solution had crystallized. Then 21.1g. of octenyl succinic anhydride was added to the crystallized mixture and the resulting mixture heated at 50°C for 5 hours to provide a homogeneous solution. The solvent was removed under vacuum, thereby providing a dark, orange-brown viscous liquid. Potentiometric titration for carboxyl ion confirmed that allyl dimethyl octenylhydroxysuccinyloxyethyl ammonium chloride had been obtained.

Ethyl acrylate (120g.), butyl acrylate (15g.) and acrylonitrile (15g.) were charged to a 4-neck resin kettle equipped with a thermometer, stirrer, nitrogen inlet and dropping apparatus. To the amount of 4.5g. of the monomeric emulsion stabilizer described in the preceding paragraph, dissolved in 425g. of $H_2O$, was added, under nitrogen, the mixture of monomers. The pH of the resulting emulsion was 4.0–4.5. After cooling to 20°C by the use of an ice bath, 15ml. of 3% $H_2O_2$ in $H_2O$ were added to the emulsion followed by dropwise addition of a reductant solution comprising 0.02g ferrous ammonium sulfate and 0.4g. ascorbic acid in 10ml. $H_2O$. Polymerization was initiated after 2.5ml. of reductant solution had been added as evidenced by an exotherm of about 29°C in 10 minutes. A total of 9ml. of reductant solution was added until completion of the polymerization as evidenced by a lack of exotherm upon the further addition of a slight amount of $H_2O_2$ and reductant. The yield of polymer was 95% of theoretical, and no coagulum formed.

EXAMPLE 2

Following the procedure of Example 1, 7.7g. of allyl chloride was added slowly, with stirring, to a solution of 8.9g. of dimethylaminoethanol in 16.6g. of acetonitrile. The reaction solution crystallized after standing 24 hours at room temperature. Then a solution of 26.7g. of n-dodecenyl succinic anhydride in 26.7g. of acetonitrile was added and the mixture maintained at 50°C for 5 hours, thereby providing a clear homogeneous solution. The solvent was removed under vacuum to yield a viscous orange liquid. Potentiometric titration for carboxyl ion confirmed that allyl dimethyl n-dodecenylhydroxysuccinyloxyethyl ammonium chloride had been obtained.

EXAMPLE 3

Dimethylaminoethanol (102g.) was added slowly at 17°C to a solution of 88.3g. of allyl chloride in 500g. of acrylonitrile. Over 90 minutes an exotherm of 26°C was observed. Then the solution was allowed to cool to 35°C at which temperature crystallization occurred, producing a 10°C exotherm. Tetrapropenyl succinic anhydride, which is an alkenyl succinic anhydride having an average of 12 carbon atoms and one carbon-carbon double bond, (310g.) was added to the crystallized mixture; after 45 minutes a clear, homogeneous solution was obtained. This solution was allowed to stand for 48 hours. Chloride ion analysis confirmed that allyl dimethyl tetrapropenylhydroxysuccinyloxyethyl ammonium chloride had been obtained.

EXAMPLE 4

Dimethylaminoethanol (35.6g.) was added slowly to a solution of 106.4g. of tetrapropenyl succinic anhydride in 160ml. of ethyl acetate. After completion of the exotherm, a dark orange liquid was obtained. Allyl bromide (12.1g.) was added to 65.5g. of this liquid. After the mixture was allowed to stand for 24 hours at room temperature, bromide ion analysis confirmed that allyl dimethyl tetrapropenylhydroxysuccinyloxyethyl ammonium bromide had been obtained.

The amount of 4g. of this compound was dissolved in 290g. of $H_2O$ and 75g. of ethyl acrylate added; the pH of the resulting emulsion was about 5. After cooling to 19°C, polymerization was initiated and maintained by the addition of 8ml. of 3% $H_2O_2$ in $H_2O$ followed by the dropwise addition of the reductant solution described in Example 1. A total of 2.9ml. of reductant solution was employed in the polymerization and the yield of polymer was 95% of theoretical.

EXAMPLE 5

A solution of 29.5g. of n-tetradodecenyl succinic anhydride in 29.5g. of acetonitrile was added to the reaction product of 8.9g. of dimethylaminoethanol and 7.7g. of allyl chloride in 16.6g. acetonitrile as described in Example 1, and the resulting mixture heated at 55°C for 4 hours. Removal of solvent under vacuum provided 42.6g. of greasy, off-white solid. Carboxyl ion analysis confirmed that allyl dimethyl n-tetradodecenylhydroxysuccinyloxyethyl ammonium chloride had been obtained.

EXAMPLE 6

Following the procedure of Example 5, 35.6g. of iso-octadecenyl succinic anhydride was added to the reaction product of dimethylaminoethanol and allyl chloride in acetonitrile. After 5 hours at 55°C, solvent was removed under vacuum to provide an orange viscous liquid. Analysis for carboxyl ion content confirmed that allyl dimethyl iso-octadecenylhydroxysuccinyloxyethyl ammonium chloride had been obtained.

A mixture of 120g. of ethyl acrylate, 15g. of butyl acrylate and 15g. of acrylonitrile in 425g. of $H_2O$ was emulsified employing 4.5g. of the allyl dimethyl isooctadecenylhydroxysuccinyloxyethyl ammonium chloride. The emulsion, which had a pH of 4.5–5.0, was cooled to slightly below room temperature. Then 15ml. of 3% $H_2O_2$ solution was added followed by the dropwise addition of the reductant solution described in the previous examples. A total of 7ml. of reductant solution was used in the polymerization; no coagulum formed and the yield of polymer was 93% of theoretical.

EXAMPLE 7

A solution of 71.2g. of iso-octadecenyl succinic anhydride in 52g. acetonitrile was added slowly to a 50% solution of 18g. dimethylaminoethanol in acetonitrile at 25°C. The reaction was exothermic and two layers formed. After stirring the reaction mixture for one hour at 25°C, the temperature was raised to 40°–50°C and the reaction mixture heated for one and one-half hours. Solvent removal under vacuum provided a viscous orange liquid. To a solution of 22.3g. of this orange liquid in 28.4g. of dimethylformamide was added 6.07g. of allyl bromide at 25°C. After 24 hours, bromide ion analysis indicated that allyl dimethyl iso-octadecenylhydroxysuccinyloxyethyl ammonium bromide had been obtained.

EXAMPLE 8

Dimethylaminoethanol (8.9g.) was added to 9.06g. of methallyl chloride in 44.6g. of acetonitrile. After allowing the mixture to stand for 24 hours at room temperature, a clear homogeneous solution was obtained. Upon the addition of 26.6g. of tetrapropenyl succinic anhydride, an exothermic reaction occurred. Solvent was removed under vacuum to provide a viscous liquid product. Analysis for carboxyl ion content confirmed that methallyl dimethyl tetrapropenylhydroxysuccinyloxyethyl ammonium chloride had been obtained.

EXAMPLE 9

Vinyl chloroacetate (6.02g.) was added to the reaction product of 4.5g. of dimethylaminoethanol and 17.8g. of isooctadodecenyl succinic anhydride in 27g. dimethylformamide. After allowing the reaction mixture to stand for 24 hours at room temperature, a homogeneous solution was obtained. Chloride ion analysis confirmed that vinylacetoxy dimethyl isooctadecenylhydroxysuccinyloxyethyl ammonium chloride had been obtained.

A mixture of 120g. of ethyl acrylate, 15g. of butyl acrylate and 15g. of acrylonitrile was emulsified with 425g. $H_2O$ and 6.6g. of the vinylacetoxy dimethyl isooctadecenylhydroxysuccinyloxyethyl ammonium chloride solution (68 percent by weight in dimethylformamide). The resulting emulsion, having a pH of 4.5, was cooled to about 18°C. Polymerization was initiated by the addition of 15ml. of 3% $H_2O_2$ in $H_2O$ followed by the dropwise addition of 2.2ml. of the reductant solution described in the previous examples. A total of 8ml. of reductant solution was employed in the polymerization. No coagulum was formed and the yield of polymer was 94% of theoretical.

EXAMPLE 10

A solution of 53.2g. of tetrapropenyl succinic anhydride in acetonitrile was added slowly with stirring, at 25°C, to a solution of 20.4g. of dimethylaminopropylamine in acetonitrile; a total of 73.6g. of acetonitrile was employed. After stirring the reaction mixture for two hours at room temperature, the solvent was removed under vacuum to provide 71.5g. of orange viscous liquid. Then a solution of 6.05g. of allyl bromide in 24.5g. of acetonitrile was added to 18.4g. of the orange viscous liquid. The resulting mixture was allowed to stand at room temperature for 5 days. Removal of the solvent under vacuum provided 23.9g. of orange-brown viscous liquid. Bromide ion analysis confirmed that allyl dimethyl tetrapropenylhydroxysuccinylaminopropyl ammonium bromide had been obtained.

A mixture of 120g. of ethyl acrylate. 15g. of butyl acrylate and 15g. of acrylonitrile in 425g. of $H_2O$ was emulsified using 4.5g. allyl dimethyl tetrapropenylhydroxysuccinylaminopropyl ammonium bromide. The resulting emulsion, having a pH of 4.5–5.0, was cooled to 18°C. Polymerization was initiated by the addition of 15ml. of 3% $H_2O_2$ in $H_2O$ followed by the addition of 1.5ml. of the reductant solution described in the previous examples. A total of 7ml. of reductant solution was required to complete the polymerization. No coagulum formed and the yield of polymer was 92% of theoretical.

EXAMPLE 11

The amount of 20.4g. of dimethylaminopropylamine was added to a 15.3g. of allyl chloride dissolved in 35.7g. of acetonitrile. The reaction was carried out at ice-bath temperature. After 24 hours at room temperature, 53.2g. of tetrapropenyl succinic anhydride was added slowly, with stirring, to the reaction solution. Solvent removal provided a product which contained 96% of the theoretical carboxyl ion content of allyl dimethyl tetrapropenylhydroxysuccinylaminopropyl ammonium chloride had been obtained.

EXAMPLE 12

Dimethylaminoethyl methacrylate (15.7g.) was added, with stirring, at room temperature to a solution of 12.5g of 2-bromoethanol in 28.2g. of acetonitrile. A slightly exothermic reaction ensued. The reaction solution was allowed to stand for 4 days. Then 26.6g. of tetrapropenyl succinic anhydride was added to the solution. A slightly exothermic reaction occurred. After allowing the reaction mixture to stand at room temperature for 24 hours, carboxyl ion analysis revealed that methacryloyloxyethyl dimethyl tetrapropenylhydroxysuccinyloxyethyl ammonium bromide had been obtained.

To 4.5g. of the above monomeric emulsion stabilizer solution (66 percent by weight in acetonitrile) was added 100g. of ethyl acrylate and 290g. of $H_2O$. The resulting emulsion, having a pH of 4.5, was cooled to 17°C and polymerization initiated by the addition of 10ml. 3% $H_2O_2$ solution followed by 2ml. of te reductant solution described in the previous examples. A total of 3ml. of reductant solution was employed in the polymerization. No coagulum formed and the yield of polymer was 95% of theoretical.

EXAMPLE 13

Following the procedure of Example 12, 11.5g. of dimethylaminoethyl vinyl ether was added at room temperature to a solution of 12.5g. of 2-bromoethanol in 24.3g. of acetonitrile. The reaction was slightly exothermic. After allowing the reaction mixture to stand at room temperature for 4 days, a clear, homogeneous solution was obtained. To this solution was added 26.8g. of tetrapropenyl succinic anhydride. After allowing this reaction mixture to stand at room temperature for 48 hours, carboxyl ion analysis indicated that vinyloxyethyl dimethyl tetrapropenylhydroxysuccinyloxyethyl ammonium bromide had been obtained.

EXAMPLE 14

Allyl chloroacetate (6.73g.) was added to the reaction product of 4.5g. of dimethylaminoethanol and 17.8g. of iso-octadodecenyl succinic anhydride in 27g. of dimethyl formamide. Chloride ion analysis confirmed that allylacetoxy dimethyl iso-octadecenylhydroxysuccinyloxyethyl ammonium chloride had been obtained.

EXAMPLE 15

A solution of 26.6g. of tetrapropenyl succinic anhydride in 25g. dimethyl formamide was added slowly with stirring, at 25°C to a solution of 13.1g. of hydroxyethylmorpholine in 20g. dimethyl formamide. The reaction was exothermic, providing a light, orange-brown homogeneous solution which contained 93% of the theoretical carboxyl ion content. Allyl bromide (10.9g.) was added to the solution and the resulting mixture allowed to stand at room temperature for 6 days. Bromide ion analysis confirmed that allyl tetrapropenylhydroxysuccinyloxyethyl morpholinium bromide had been obtained.

EXAMPLE 16

A solution of 26.6g. of tetrapropenyl succinic anhydride in 25g. dimethylformamide was added slowly, with stirring, at 25°C to a solution of 8.9g. of dimethylaminoethanol in 10g. of dimethylformamide. The reaction was exothermic, providing, after 24 hours, a clear homogeneous solution which contained 100% of the theoretical carboxyl ion content. To the above solution was added, at 25°C with stirring, an equimolar amount of 2-bromoethanol. The reaction was slightly exothermic. After allowing te reaction mixture to stand for five days at 25°C and then for 3 ½ hours at 45°–50°C, 82% of the theoretical bromide ion content was determined. To this solution was added an equimolar amount of maleic anhydride; the addition was carried out with stirring at room temperature. After 24 hours at room temperature, carboxyl ion analysis indicated that 2-(4-hydroxymaleoyl)-oxyethyldimethyldodecenylhydroxysuccinyloxyethyl ammonium bromide had been obtained.

What is claimed is:

1. A compound having the formula

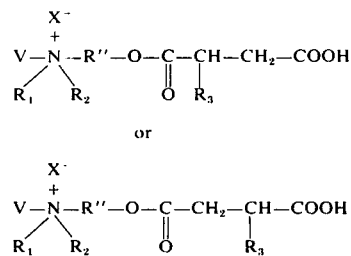

wherein V is

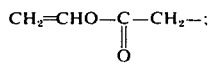

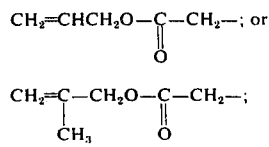

R'' is ethylene, propylene, isopropylene, 2-hydroxypropylene, acetoxypropylene or —CH$_2$—CHR$_4$(O—CH$_2$—CHR$_4$)$_n$ wherein $n$ is zero to 4 and R$_4$ is hydrogen or methyl;

R$_1$ and R$_2$ are independently selected from the group consisting of alkyl and hydroxyalkyl of 1 to 7 carbon atoms;

R$_3$ is a lipophilic aliphatic hydrocarbon group having from 7 to 28 carbon atoms; and X$^-$ is halide, alkyl sulfate wherein the alkyl moiety has 1 to 4 carbon atoms, or toluene sulfonate.

2. The compound of claim 1 having the name vinylacetoxy dimethyl iso-octadecenylhydroxysuccinyloxyethyl ammonium chloride.

3. The compound of claim 1 having the name allylacetoxy dimethyl iso-octadecenylhydroxysuccinyloxyethyl ammonium cloride.

* * * * *